US012806188B2

(12) United States Patent
Komeno et al.

(10) Patent No.: US 12,806,188 B2
(45) Date of Patent: Nov. 24, 2026

(54) CORONAVIRUS INFECTION THERAPEUTIC AGENT FORMED THROUGH COMBINATION OF PYRAZINE DERIVATIVE AND ANOTHER CORONA VIRUS INFECTION THERAPEUTIC DRUG

(71) Applicant: FUJIFILM TOYAMA CHEMICAL CO., LTD., Chuo-ku (JP)

(72) Inventors: Takashi Komeno, Toyama (JP); Nozomi Yamashita, Toyama (JP)

(73) Assignee: FUJIFILM TOYAMA CHEMICAL CO., LTD., Chuo-ku (JP)

( * ) Notice: Subject to any disclaimer, the term of this patent is extended or adjusted under 35 U.S.C. 154(b) by 840 days.

(21) Appl. No.: 17/997,422

(22) PCT Filed: Apr. 27, 2021

(86) PCT No.: PCT/JP2021/016737
§ 371 (c)(1),
(2) Date: Oct. 28, 2022

(87) PCT Pub. No.: WO2021/221043
PCT Pub. Date: Nov. 4, 2021

(65) Prior Publication Data

US 2023/0210848 A1 Jul. 6, 2023

(30) Foreign Application Priority Data

Apr. 30, 2020 (JP) ................................ 2020-080731

(51) Int. Cl.
*A61K 31/4965* (2006.01)
*A61K 31/706* (2006.01)
*A61K 45/06* (2006.01)
*A61P 31/14* (2006.01)

(52) U.S. Cl.
CPC ........ *A61K 31/4965* (2013.01); *A61K 31/706* (2013.01); *A61K 45/06* (2013.01); *A61P 31/14* (2018.01)

(58) Field of Classification Search
None
See application file for complete search history.

(56) References Cited

U.S. PATENT DOCUMENTS

| | | | | |
|---|---|---|---|---|
| 8,759,354 | B2 * | 6/2014 | Maekawa | A61K 31/215 514/459 |
| 2017/0100385 | A1 | 4/2017 | Washburn | |
| 2018/0207145 | A1 | 7/2018 | Washburn | |

FOREIGN PATENT DOCUMENTS

| | | | |
|---|---|---|---|
| EP | 4 321 163 | A1 | 2/2024 |
| JP | 2002-518455 | A | 6/2002 |
| JP | 2008-540600 | A | 11/2008 |
| JP | 2012-512883 | A | 6/2012 |
| JP | 2015-28087 | A | 2/2015 |
| JP | 2015-525221 | A | 9/2015 |
| JP | 2016-65037 | A | 4/2016 |
| JP | 2016-512833 | A | 5/2016 |
| JP | 2016-539944 | A | 12/2016 |
| JP | 2017-524339 | A | 8/2017 |
| JP | 2017-178913 | A | 10/2017 |
| WO | WO 99/66942 | A1 | 12/1999 |
| WO | WO 2006/122819 | A1 | 11/2006 |
| WO | WO 2010/123527 | A2 | 10/2010 |
| WO | WO 2013/185093 | A1 | 12/2013 |
| WO | WO 2014/151085 | A1 | 9/2014 |
| WO | WO 2015/080973 | A1 | 6/2015 |
| WO | WO 2015/173701 | A2 | 11/2015 |
| WO | WO 2015/179535 | A1 | 11/2015 |
| WO | WO 2016/172205 | A1 | 10/2016 |
| WO | WO 2020/138067 | A1 | 7/2020 |
| WO | WO 2021/154687 | A1 | 8/2021 |

OTHER PUBLICATIONS

Chou, Ting-Chao, Pharmacological Reviews, 58(3), 621-681 (Year: 2006).*

De Clercq et al., Clinical Microbiology Reviews, 29(3), 695-747 (Year: 2016).*

Furuta et al., Antiviral Research, 100, 446-454 (Year: 2013).*

Lanevski et al., Drug Discovery Today, 24(5), 1224-1228 (Year: 2019).*

Wang et al., Cell Research (Feb. 4, 2020), 30, 369-271 (Year: 2020).*

Extended European Search Report issued Jul. 29, 2024, in corresponding European Patent Application No. 21795973.3, 30 pages.

Harrison Charlotte: "Coronavirus puts drug repurposing on the fast track", Nature Biotechnology, Nature Publishing Group US, New York, vol. 38, No. 4, Feb. 27, 2020, pp. 379-381, XP037154992, ISSN: 1087-0156, DOI: 10.1038/D41587-020-00003-1, [retrieved on Feb. 27, 2020].

Yan Lou et al: "Clinical Outcomes and Plasma Concentrations of Baloxavir Marboxil and Favipiravir in COVID-19 Patients: An Exploratory Randomized, Controlled Trial", European Journal of Pharmaceutical Sciences, Elsevier Amsterdam, NL, vol. 157, Oct. 25, 2020, XP086422279, ISSN: 0928-0987, DOI: 10.1016/J.EJPS.2020.105631 [retrieved on Oct. 25, 2020].

Wang, C, et al., "A novel coronavirus outbreak of global health concern", Lancet, Feb. 2020, vol. 395, pp. 470-473.

Coronaviridae Study Group of the International Committee on Taxonomy of Viruses, "The species Severe acute respiratory syndrome-related coronavirus: classifying 2019-nCoV and naming it SARS-CoV-2", Nature Microbiology, Mar. 2, 2020., PubMed PMID: 32123347, pp. 536-544.

(Continued)

*Primary Examiner* — George W Kosturko
*Assistant Examiner* — Jason M. Nolan
(74) *Attorney, Agent, or Firm* — Oblon, McClelland, Maier & Neustadt, L.L.P.

(57) ABSTRACT

A pharmaceutical composition for treating coronavirus infection which includes a combination of a pyrazine derivative its salt and another therapeutic agent for treating coronavirus infection.

2 Claims, No Drawings

(56) References Cited

OTHER PUBLICATIONS

"Coronavirus disease 2019 (COVID-19) situation reports—62", (Mar. 22, 2020), [Internet]. Geneva: World Health Organization. Available from: https://www.who.int/docs/default-source/coronaviruse/situation-reports/20200322-sitrep-62-covid-19.pdf?sfyrsn=f7764c46_2, 10 pages.
Liu, C., et al., "Research and Development on Therapeutic Agents and Vaccines for COVID-19 and Related Human Coronavirus Diseases", ACS Central Science (2020), 6(3), pp. 315-331.
Cai, Q. et al., "Experimental Treatment with Favipiravir for COVID-19: An Open-Label Control Study", Engineering, Mar. 6, 2020, pp. 1192-1198, Abstract, 第1193ページ左欄第3パラ,第1193ページ右欄第2パラ, Table2 1-20.
Choy, K.T. et al., "Remdesivir, lopinavir, emetine, and homoharringtonine inhibit SARS-CoV-2 replication in vitro", Antiviral Research, Apr. 3, 2020, 178, 104786, pp. 1-5.
Beck, B. R. et al., "Predicting commercially available antiviral drugs that may act on the novel coronavirus (SARS-CoV-2) through a drug-target interaction deep learning model", Computational and Structural Biotechnology Journal, Mar. 18, 2020, pp. 784-790.
Williamson, B.N. et al., "Clinical benefit of remdesivir in rhesus macaques infected with SARS-CoV-2", bioRxiv, Apr. 22, 2020, pp. 1-21, DOI: 10.1101/2020.04.15.043166.
Wang, M. et al., "Remdesivir and chloroquine effectively inhibit the recently emerged novel coronavirus (2019-nCov) in vitro", Cell Research, Feb. 30, 2020(3), pp. 269-271.
Grein, J. et al., "Compassionate Use of Remdesivir for Patients with Severe Covid-19", The New England Journal of Medicine, Apr. 10, 2020, p. 1-10, doi: 10.1056/NEJMoa2007016.
Vlasak, R et al., "Influenza C Virus Esterase: Analysis of Catalytic Site, Inhibition, and Possible Function", Journal of Virology, May 1989, vol. 63 No. 5, pp. 2056-2062.
Matsuyama, S. et al., "The inhaled corticosteroid ciclesonide blocks coronavirus RNA replication by targeting viral NSP15", bioRxiv, 2020.03, doi:https://doi.org/10.1101/2020.03.11.987016, 9 pages.
Johansen, L.M. et al., "FDA-Approved Selective Estrogen Receptor Modulators Inhibit Ebola Virus Infection", Science Translational Medicine, 2013, vol. 5, No. 190, 190ra79, p. 1-13.
Xu, X. et al., "Effective treatment of severe COVID-19 patients with Tocilizumab", China XiV, Mar. 2020, vol. 21, p. 1-10.
Wang, D.et al., "An overview of the safety, clinical application and antiviral research of the COVID-19 therapeutics", Journal of Infection and Public Health, Jul. 13, 2020, pp. 1405-1414.
Sanders, J. M. et al., "Pharmacologic treatments for coronavirus disease 2019(COVID-19)", JAMA, May 2020, 323(18) , pp. 1824-1836.
International Search Report issued Jul. 20, 2021 in PCT/JP2021/016737, 9 pages.
Partial Supplementary European Search Report issued Apr. 16, 2024 in European Patent Application No. 21795973.3, 26 pages.
Anonymous, "Favipiravir Combined With Tocilizumab in the Treatment of Corona Virus Disease 2019," Clinicaltrials.gov, retrieved from the internet: URL: https://clinicaltrials.gov/study/NCT04310228?tab=history&a=1, Mar. 14, 2020, XP093146563, 17 pages.
Anonymous, "Fight COVID-19 Trial (FIGHT-COVID-19)," Clinicaltrials.gov, retrieved from the internet: URL: https://clinicaltrials.gov/study/NCT04303299?tab=history&a=3, Mar. 23, 2020, XP093146558, 19 pages.
Ahktar, J., "COVID19 inhibitors: A prospective therapeutics," Bioorganic Chemistry, vol. 101, Jun. 17, 2020, XP086227754, 9 pages.
Khamis, F. et al., "Randomized controlled open label trial on the use of favipiravir combined with inhaled interferon beta-1b in hospitalized patients with moderate to severe COVID-19 pneumonia," International Journal of Infectious Diseases, vol. 102, Nov. 9, 2020, XP086421742, pp. 538-543.
Bobrowski et al., "Synergistic and Antagonistic Drug Combinations against SARS-CoV-2," Molecular Therapy, vol. 29, pp. 873-885, (2021).

* cited by examiner

CORONAVIRUS INFECTION THERAPEUTIC AGENT FORMED THROUGH COMBINATION OF PYRAZINE DERIVATIVE AND ANOTHER CORONA VIRUS INFECTION THERAPEUTIC DRUG

TECHNICAL FIELD

The present invention relates to a therapeutic agent for coronavirus infection comprising a combination of a pyrazine derivative or a salt thereof and one or more other therapeutic agents for coronavirus infection.

BACKGROUND ART

The novel coronavirus (SARS-CoV-2) first reported in China at the end of 2019 (Non-patent Literature 1) is an RNA virus belongs to the family coronaviridae, order nidovirales (Non-patent Literature 2). When infected with this virus, fever and acute respiratory symptoms including cough and dyspnea develop (Non-patent Literature 1), and when the condition is exacerbated, pneumonia develops. As of Mar. 22, 2020, more than 290,000 patients infected with SARS-CoV-2 (COVID-19) and more than 12,000 deaths have been reported in the world. In Japan, 1,046 COVID-19 infection patients have been reported and of them, 36 deaths have been confirmed (Non-patent Literature 3).

As substances that may be effective for the treatment of COVID-19, baricitinib, lopinavir, ritonavir, darunavir, favipiravir (a pyrazine derivative), remdesivir, ribavirin, and the like have been reported (Non-patent Literature 4). However, no studies have systematically evaluated effects of combination use of two or more of these against coronavirus.

PRIOR ART DOCUMENTS

Non-Patent Document

Non-Patent Literature 1: "Senryou Kagaku" (Dye Chemistry in Japanese), Yutaka Hosoda, Gihodo Co., Ltd., 1957, p. 621 Wang C, Horby P W, Hayden F G, Gao G F. A novel coronavirus outbreak of global health concern. Lancet. 2020; 395:470-3.

Non-patent Literature 2: Coronaviridae Study Group of the International Committee on Taxonomy of Viruses. The species Severe acute respiratory syndrome-related coronavirus: classifying 2019-nCoV and naming it SARS-CoV-2. Nat Microbiol. 2020 Mar. 2. PubMed PMID: 32123347.

Non-patent Literature 3: Coronavirus disease 2019 (COVID-19) situation reports-62 (22 Mar. 2020). [Internet]. Geneva: World Health Organization. Available from: https://www.who.int/docs/default-source/coronaviruse/situation-reports/20200322-sitrep-62-covid-19.pdf?sfvrsn=f7764c46_2

Non-patent Literature 4: ACS Central Science (2020), 6(3), 315-331

SUMMARY OF INVENTION

Problem to be Solved by the Invention

An object of the present invention is to provide a novel combination of substances showing effects against coronavirus.

Means to Solve the Problem

Under the above-described circumstances, the present inventors have found as a result of extensive studies that the antiviral activity against coronavirus is enhanced if a pyrazine derivative represented by general formula [1]

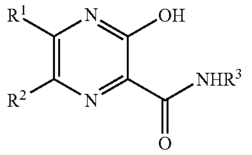

[1]

(wherein $R^1$ and $R^2$, identical or different, each represent a hydrogen atom or a halogen atom; and $R^3$ represents a hydrogen atom or an amino protecting group) or a salt thereof is used in combination with another therapeutic agent for coronavirus infection, and accomplished the present invention.

Specifically, the present invention provides the following: [1]

A pharmaceutical composition for treating coronavirus infection, comprising a pyrazine derivative represented by the following general formula:

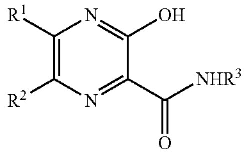

[1]

(wherein $R^1$ and $R^2$, identical or different. each represent a hydrogen atom or a halogen atom; and $R^3$ represents a hydrogen atom or an amino protecting group) or a salt thereof and one or more therapeutic agent for coronavirus infection selected from the following (1) to (19):

(1) Interferon;
(2) Nucleic acid analogue;
(3) Protease inhibitor;
(4) Furin convertase cleavage inhibitor;
(5) Reverse transcriptase inhibitor and/or other RNA polymerase inhibitor;
(6) Neuraminidase inhibitor;
(7) Angiotensin II receptor blocker;
(8) Endosome fusion inhibitor and/or endosome alkalinizer;
(9) AAK1, GAK, and clathrin A,B,C (endocytosis) inhibitor
(10) Hemagglutinin esterase inhibitor;
(11) Cytokine or inflammation inhibitor or modifier;
(12) Cathepsin B inhibitor;
(13) Cathepsin L inhibitor;
(14) Helicase nsp13 inhibitor;
(15) MBL2 gene agonist;
(16) TP53 inhibitor;
(17) Selective estrogen receptor modifier;
(18) Corticosteroid; and
(19) Amantadine, foscarnet, triazavirin, umifenovir, rapamycin, everolimus, nitazoxanide, tizoxanide, caraphenol A, ivermectin, VIR-2703, tocilizumab, bamlanivimab, etesebimab, kasiribimab/imdebimab, AZD7422, VIR-7831, VIR-7832, or BI 767551.

[2]

The pharmaceutical composition according to [1], wherein the interferon is interferon α-2A, interferon α-2B, interferon α-n1, interferon α-n3, interferon β-1a, or interferon β-1b.

[3]

The pharmaceutical composition according to [1], wherein the nucleic acid analogue is acyclovir, ganciclovir, ribavirin, or taribavirin.

[4]

The pharmaceutical composition according to [1], wherein the protease inhibitor is indinavir, nelfinavir, saquinavir, camostat, lopinavir/ritonavir combination (brand name, Kaletra), epigallocatechin gallate, kaempferol-7-glucoside, mycophenolic acid, darunavir, mercaptopurine, disulfiram, nafamostat, or PF-07321332.

[5]

The pharmaceutical composition according to [1], wherein the furin convertase cleavage inhibitor is tenofovir disoproxil, dolutegravir, boceprevir, andrographolide, luteolin, or baicalein.

[6]

The pharmaceutical composition according to [1], wherein the reverse transcriptase inhibitor and/or other RNA polymerase inhibitor is remdesivir, sofosbuvir, dactinomycin, galidesivir, baloxavir marboxil, molnupiravir, sangibamycin, or AT-527.

[7]

The pharmaceutical composition according to [1], wherein the neuraminidase inhibitor is oseltamivir or zanamivir.

[8]

The pharmaceutical composition according to [1], wherein the angiotensin II receptor blocker is valsartan, telmisartan, losartan, irbesartan, azilsartan, olmesartan, or emodin.

[9]

The pharmaceutical composition according to [1], wherein the endosome fusion inhibitor and/or endosome alkalinizer is baicalin, chloroquine, hydroxychloroquine, griffithsin, quinine, or lactoferrin.

[10]

The pharmaceutical composition according to [1], wherein the AAK1, GAK, and clathrin A,B,C (endocytosis) inhibitor is baricitinib, sunitinib, erlotinib, fedratinib, gefitinib, or silibinin.

[11]

The pharmaceutical composition according to [1], wherein the hemagglutinin esterase inhibitor is 3,4-dichloroisocoumarin.

[12]

The pharmaceutical composition according to [1], wherein the cytokine or inflammation inhibitor or modifier is ligustrazine, statin, melatonin, eplerenone, or methylprednisolone.

[13]

The pharmaceutical composition according to [12], wherein the cathepsin B inhibitor is salvianolic acid B.

[14]

The pharmaceutical composition according to [1], wherein cathepsin L inhibitor is MOL736, chelidocystatin, astaxanthin, curcumin, or vitamin D.

[15]

The pharmaceutical composition according to [1], wherein the helicase nsp13 inhibitor is valsartan, bananin, iodobananin, vanillinbananin, eubananin, or silvestrol.

[16]

The pharmaceutical composition according to [1], wherein the MBL2 gene agonist is β-glucan or vitamin A.

[17]

The pharmaceutical composition according to [1], wherein the TP53 inhibitor is vitexin or gossypol.

[18]

The pharmaceutical composition according to [1], wherein the selective estrogen receptor modifier is toremifene or equilin.

[19]

The pharmaceutical composition according to [1], wherein the corticosteroid is ciclesonide or dexamethasone.

[20]

The pharmaceutical composition according to [1], wherein the one or more therapeutic agent for coronavirus infection is a reverse transcriptase inhibitor and/or other RNA polymerase inhibitor.

The present invention further provides the following:

[A]

A method for treating coronavirus infection, comprising administration of a pyrazine derivative represented by general formula [1]:

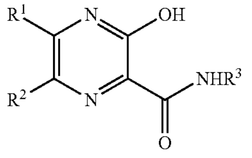

[1]

(wherein $R^1$ and $R^2$, identical or different, each represent a hydrogen atom or a halogen atom; and $R^3$ represents a hydrogen atom or an amino protecting group) or a salt thereof and another therapeutic agent for coronavirus infection to manufacture a therapeutic agent for coronavirus infection.

[B]

Use of a pyrazine derivative represented by general formula [1]:

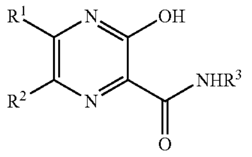

[1]

(wherein $R^1$ and $R^2$, identical or different, each represent a hydrogen atom or a halogen atom; and $R^3$ represents a hydrogen atom or an amino protecting group) or a salt thereof and another therapeutic agent for coronavirus infection to manufacture a therapeutic agent for coronavirus infection.

[C]

A combination of a pyrazine derivative represented by general formula [1]

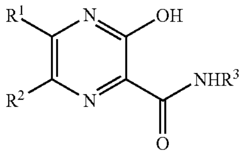

[1]

(wherein $R^1$ and $R^2$, identical or different, each represent a hydrogen atom or a halogen atom; and $R^3$ represents a hydrogen atom or an amino protecting group) or a salt thereof and another therapeutic agent for coronavirus infection to use in the treatment of coronavirus infection.

Advantageous Effects of Invention

A therapeutic agent for coronavirus infection comprising a combination of a pyrazine derivative or a salt thereof and another therapeutic agent for coronavirus infection is useful for treatments such as therapeutic or prophylactic treatment of coronavirus infection.

EMBODIMENTS FOR CARRYING OUT THE INVENTION

The present invention will be described in detail below.

In this specification, a range of numerical values represented using "to" means a range including the numerical values before and after "to" as the minimum value and the maximum value, respectively.

The halogen atom means a fluorine atom, chlorine atom, bromine atom, or iodine atom. The $C_{1-6}$ alkyl group means a straight or branched $C_{1-6}$ alkyl group such as a methyl, ethyl, propyl, isopropyl, butyl, sec-butyl, isobutyl, tert-butyl, pentyl, isopentyl, 2-methylbutyl, 2-pentyl, 3-pentyl, or hexyl group.

The amino protecting groups include all groups that can be used as a usual amino protecting group, and examples thereof include groups listed in W. Greene et al., Protective Groups in Organic Synthesis Fifth Edition, pp. 895-1193, 2014, John Wiley & Sons, Inc.

Specifically, examples thereof include an acyl group, alkyloxycarbonyl group, arylalkyloxycarbonyl group, aryloxycarbonyl group, arylalkyl group, alkoxyalkyl group, arylalkyloxyalkyl group, arylthio group, alkylsulfonyl group, arylsulfonyl group, dialkylaminoalkylidene group, arylalkylidene group, nitrogen-containing heterocyclic alkylidene group, cycloalkylidene group, diarylphosphoryl group, diarylalkylphosphoryl group, oxygen-containing heterocyclic alkyl group, and substituted silyl group.

Examples of a salt of the compound represented by general formula [1] include commonly known salts in a hydroxyl group. Examples thereof include salts with alkali metals such as sodium and potassium; salts with alkaline earth metals such as calcium and magnesium; ammonium salts; and salts with nitrogen-containing organic nucleotides such as trimethylamine, triethylamine, tributylamine, N-methylpiperidine, N-methylmorpholine, diethylamine, dicyclohexylamine, procaine, dibenzylamine, N-benzyl-β-phenethylamine, 1-efenamine, and N,N'-dibenzylethylenediamine. Preferred examples of salts include pharmacologically acceptable salts, and salts with sodium are more preferred.

In the compound represented by general formula [1], preferably, $R^1$ is a hydrogen atom; $R^2$ is a fluorine atom; and $R^3$ is a hydrogen atom. This compound is preferably T-705 (favipiravir).

Alternatively, in the compound represented by general formula [1], preferably, $R^1$ is a hydrogen atom; $R^2$ is a hydrogen atom; and $R^3$ is a hydrogen atom. Preferably, this compound is T-1105.

The compound represented by general formula [1] is manufactured by using methods known per se in combination. For example, it can be manufactured by the manufacturing methods described in International Publication No. WO 00/10569.

The therapeutic agent for coronavirus infection means a substance showing effect in therapeutic or prophylactic treatment of coronavirus infection by a certain mechanism of action, such as inhibition of proliferation of coronavirus in the host cell, inhibition of entry of coronavirus into the host cell, inhibition of egress of coronavirus out of the host cell, activation of the body's immune function, suppression of inflammation, and suppression of cytokine storm, and examples thereof include substances listed in the following (1) to (19):

(1) Interferon;
(2) Nucleic acid analogue;
(3) Protease inhibitor;
(4) Furin convertase cleavage inhibitor;
(5) Reverse transcriptase inhibitor and/or RNA polymerase inhibitor;
(6) Neuraminidase inhibitor;
(7) Angiotensin II receptor blocker;
(8) Endosome fusion inhibitor and/or endosome alkalinizer
(9) AAK1, GAK, or clathrin A,B,C (endocytosis) inhibitor;
(10) Hemagglutinin esterase inhibitor;
(11) Cytokine or inflammation inhibitor or modifier;
(12) Cathepsin B inhibitor;
(13) Cathepsin L inhibitor;
(14) Helicase nsp13 inhibitor;
(15) MBL2 gene agonist;
(16) TP53 inhibitor;
(17) Selective estrogen receptor modifier;
(18) Corticosteroid; and
(19) Other drugs.

Examples of the interferon include interferon α-2A, interferon α-2B, interferon α-n1, interferon α-n3, interferon β-1a, and interferon β-1b. It is sufficient to manufacture an interferon by using methods known per se in combination or to use a commercially available one.

Examples of the nucleic acid analogue include acyclovir, ganciclovir, ribavirin, and taribavirin. It is sufficient to manufacture a nucleic acid analogue by using methods known per se in combination or to use a commercially available one.

Examples of the protease inhibitor include indinavir, nelfinavir, saquinavir, camostat, lopinavir/ritonavir combination (brand name, Kaletra), epigallocatechin gallate, kaempferol-7-glucoside, mycophenolic acid, darunavir, mercaptopurine, disulfiram, nafamostat, and PF-07321332. It is sufficient to manufacture a protease inhibitor by using methods known per se in combination or to use a commercially available one.

Examples of the furin convertase cleavage inhibitor include tenofovir disoproxil, dolutegravir, boceprevir, andrographolide, luteolin, and baicalein. It is sufficient to manufacture a furin convertase cleavage inhibitor by using methods known per se in combination or to use a commercially available one.

Examples of the reverse transcriptase inhibitor and/or RNA polymerase inhibitor include remdesivir, sofosbuvir, dactinomycin, galidesivir, baloxavir marboxil, molnupiravir, sangibamycin and, AT-527. It is sufficient to manufacture a reverse transcriptase inhibitor and/or RNA polymerase inhibitor by using methods known per se in combination or to use a commercially available one.

Examples of the neuraminidase inhibitor include oseltamivir and zanamivir. It is sufficient to manufacture a neuraminidase inhibitor by using methods known per se in combination or to use a commercially available one.

Examples of the angiotensin II receptor blocker include valsartan, telmisartan, losartan, irbesartan, azilsartan, olmesartan, and emodin. It is sufficient to manufacture an angiotensin II receptor blocker by using methods known per se in combination or to use a commercially available one.

Examples of the endosome fusion inhibitor and/or endosome alkalinizer include baicalin, chloroquine, hydroxychloroquine, griffithsin, quinine, and lactoferrin. It is sufficient to manufacture an endosome fusion inhibitor and/or endosome alkalinizer by using methods known per se in combination or to use a commercially available one.

Examples of the AAK1, GAK, or clathrin A,B,C (endocytosis) inhibitor include baricitinib, sunitinib, erlotinib, fedratinib, gefitinib, and silibinin. It is sufficient to manufacture AAK1, GAK, or a clathrin A,B,C (endocytosis) inhibitor by using methods known per se in combination or to use a commercially available one.

Examples of the hemagglutinin esterase inhibitor include 3,4-dichloroisocoumarin. It is sufficient to manufacture a hemagglutinin esterase inhibitor by using methods known per se in combination or to use a commercially available one.

Examples of the cytokine or inflammation inhibitor or modifier include ligustrazine, statin, melatonin, eplerenone, and methylprednisolone. It is sufficient to manufacture a cytokine or inflammation inhibitor or modifier by using methods known per se in combination or to use a commercially available one.

Examples of the cathepsin B inhibitor include salvianolic acid B. It is sufficient to manufacture a cathepsin B inhibitor by using methods known per se in combination or to use a commercially available one.

Examples of the cathepsin L inhibitor include MOL736, chelidocystatin, astaxanthin, curcumin, and vitamin D. It is sufficient to manufacture a cathepsin L inhibitor by 30 using methods known per se in combination or to use a commercially available one.

Examples of the helicase nsp13 inhibitor include valsartan, bananin, iodobananin, vanillinbananin, eubananin, and silvestrol. It is sufficient to manufacture a helicase nsp13 inhibitor by using methods known per se in combination or to use a commercially available one.

Examples of the MBL2 gene agonist include β-glucan and vitamin A. It is sufficient to manufacture an MBL2 gene agonist by using methods known per se in combination or to use a commercially available one.

Examples of the TP53 inhibitor include vitexin and gossypol. It is sufficient to manufacture a TP53 inhibitor by using methods known per se in combination or to use a commercially available one.

Examples of the selective estrogen receptor modifier include toremifene and equilin. It is sufficient to manufacture a selective estrogen receptor modifier by using methods known per se in combination or to use a commercially available one.

Examples of the corticosteroid include ciclesonide and dexamethasone. It is sufficient to manufacture a corticosteroid by using methods known per se in combination or to use a commercially available one.

Examples of the other drugs include amantadine, foscarnet, triazavirin, umifenovir, rapamycin, everolimus, nitazoxanide, tizoxanide, caraphenol A, ivermectin, VIR-2703, tocilizumab, bamlanivimab, etesebimab, kasiribimab/imdebimab, AZD7422, VIR-7831, VIR-7832, and BI 767551. It is sufficient to manufacture amantadine, foscarnet, triazavirin, umifenovir, rapamycin, everolimus, nitazoxanide, tizoxanide, caraphenol A, ivermectin, VIR-2703, tocilizumab, bamlanivimab, etesebimab, kasiribimab/imdebimab, AZD7422, VIR-7831, VIR-7832, and BI 767551. by using methods known per se in combination or to use commercially available ones.

In the present invention, a pyrazine derivative and another therapeutic agent for coronavirus infection are used in combination. The combination encompasses an embodiment of administering a pyrazine derivative and another therapeutic agent for coronavirus infection simultaneously, separately, or in a specific order (combination use) and an embodiment as a mixture (a combination drug).

Specifically, the combination use does not mean only an embodiment of administering a pyrazine derivative or a salt thereof and another therapeutic agent for coronavirus infection at one time, but also encompasses an embodiment of administering a pyrazine derivative or a salt thereof and another therapeutic agent for coronavirus infection during one dosing regimen. The routes of administration of a pyrazine derivative or a salt thereof and another therapeutic agent for coronavirus infection may be identical to or different from each other.

It is sufficient to select an amount ratio of a pyrazine derivative or a salt thereof and another therapeutic agent for coronavirus infection, such that both compounds exhibit their effects additively or synergistically, and an amount ratio in which both compounds can exhibit their effects synergistically is preferred. An amount ratio (molar ratio) of a pyrazine derivative or a salt thereof and another therapeutic agent for coronavirus infection is preferably 1:500 to 500:1, more preferably 1:200 to 200:1, yet more preferably 1:50 to 50:1, and further preferably 1:10 to 10:1.

When the pyrazine derivative or a salt thereof and another therapeutic agent for coronavirus infection of the present invention is used, pharmaceutical aids usually used for formulation, such as excipients, carriers, and diluents, may be suitably added, and these compounds can be formulated into a form such as tablet, capsule, powder, syrup, granule, pill, suspension, emulsion, solution, powder formulation, suppository, eye drop, nasal drop, ear drop, patch, ointment, or injection by a usual method.

When a pyrazine derivative or a salt thereof and another therapeutic agent for coronavirus infection are used as a combination drug, it is sufficient to mix and homogenize them during the process of the above-mentioned formulation to obtain a suitable formulations.

The route of administration of the therapeutic agent for coronavirus infection of the present invention is not particularly limited, and it can be administered intravenously, orally, intramuscularly, subcutaneously, by inhalation, by aerosolization, or other routes of administration. The pyrazine derivative or a salt thereof may be administered with another therapeutic agent for coronavirus infection simultaneously or in a specific order.

The administration method, dose, and number of doses of the pyrazine derivative or a salt thereof of the present invention can be selected suitably depending on the patient's age, body weight, and symptoms. The adult dose for oral or parenteral (e.g., injection, drip infusion, and rectal administration) administration of a pyrazine derivative or a salt thereof, an active ingredient, is usually 10 to 50,000 mg or preferably 200 to 24,000 mg, which can be administered once a day (QD) or divided into a several doses a day. It is typical that administration is preferably repeated, as necessary, while being monitored. Specifically, for adults, it is sufficient to be administered at 100 to 6,000 mg QD, twice a day (BID), three times a day (TID), or four times a day (QID) on Day 1 and at 100 to 6,000 mg QD, BID, TID, or QID on Day 2 and thereafter. Preferably, the dose on Day 1 (a loading dose) is higher than the dose on Day 2 and thereafter, and the dose on Day 1 is 1.5 times or higher, two times or higher, three times or higher, four times or higher, or five times or higher than the dose on Day 2 and thereafter.

More specifically, it is sufficient to be administered at 1,000 to 5,000 mg QD, BID, TID, or QID on Day 1 and at 400 to 2,400 mg QD, BID, TID, or QID on Day 2 and thereafter. The adult dosage is preferably 1,600 mg BID on Day 1 and 600 mg BID on Day 2 and thereafter, 1,800 mg BID on Day 1 and 800 mg BID on Day 2 and thereafter, or 1,800 mg BID on Day 1 and 1000 mg BID on Day 2 and thereafter, more preferably 1,800 mg BID on Day 1 and 800 mg BID on Day 2 and thereafter.

The second dose is administered preferably with an interval of at least 4 hours, more preferably with an interval at least 6 hours, after the first dose.

The duration of administration is suitably determined depending on change over time in symptoms, and for example, can be selected from up to 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, and 31 days and 1 month, 2 months, and 3 months. Up to 10 days, 13 days, 14 days, and 22 days are preferred, and up to 14 days is more preferred. For prophylactic treatment, it is recommended to continue treatment during the period in which the infection risk is high.

The half maximal effective concentration (EC50) of T-705 included in the pyrazine derivatives of the present invention against SARS-CoV-2 was 61.88 μM in a study using Vero E6 cells (Wang M, Cao R, Zhang L, Yang X, Liu J, Xu M, et al. Remdesivir and chloroquine effectively inhibit the recently emerged novel coronavirus [2019-nCoV] in vitro. Cell Res. 2020; 30:269-71.). Since this concentration is equivalent to 9.72 μg/mL, the pyrazine derivative or a salt thereof is preferably administered, such that a blood concentration will be 9.72 μg/mL or higher. However, this shall not apply to the embodiments of the present invention that can be expected to have a synergistic effect.

The administration method, dose, and number of doses of the other therapeutic agent for coronavirus infection of the present invention can be suitably selected depending on the patient's age, body weight, and symptoms. They are preferably selected on the basis of known clinical study protocols and results. Specific examples thereof include the following:

When hydroxychloroquine is used, it is sufficient to be administered, for example, at 800 mg BID on Day 1 and at 400 mg BID on Day 2 and thereafter for up to Day 10 or at 1,200 mg divided into QID for 5 to 10 days; as a sulfate, at 800 mg BID on Day 1 and at 400 mg BID on Days 2 to 5 or at 600 mg BID on Day 1 and at 400 mg BID on Days 2 to 7.

When a lopinavir/ritonavir combination is used, it is sufficient to administer, for example, lopinavir at 200 mg/ritonavir at 100 mg BID for 7 to 10 days, lopinavir at 400 mg/ritonavir at 100 mg QD for up to 14 days, lopinavir at 400 mg/ritonavir at 100 mg BID for up to 14 days, or lopinavir at 400 mg/ritonavir at 200 mg BID for 5 to 14 days.

When ciclesonide is used, it is sufficient to administer, for example, ciclesonide at 320 μg for inhalation every 12 hours for up to 14 days or ciclesonide at 200 μg for inhalation every 12 hours for up to 14 days.

When remdesivir is used, it is sufficient to be administered, for example, at 200 mg QD on Day 1 and at 100 mg QD on Days 2 to 10, which can be extended to Day 13, at 200 mg QD on Day 1 and at 100 mg QD on Days 2 to 5, or at 400 mg BID on Day 1 and at 400 mg QD for 2 to 11 days; and at 5 mg/kg QD on Day 1 and at 2.5 mg/kg QD for Days 2 to 10, which can be extended to Day 13, for children with body weight lower than 40 kg.

When molnupiravir is used, it is sufficient to be administered, for example, at 200 mg, 400 mg, 600 mg, 800 mg, 1000 mg, 1200 mg, 1400 mg, 1600 mg, 1800 mg, or 2000 mg BID for 5 days. It is administrated preferably at 800 mg BID for 5 days.

The therapeutic agent for coronavirus infection of the present invention is useful for treatments such as therapeutic or prophylactic treatment of coronavirus infection.

The term "coronavirus" used in this specification means an RNA virus belonging to the family coronaviridae, the order nidovirales. Coronavirus infection is an infectious disease caused by coronavirus. The term "novel coronavirus" means a newly identified and reported novel coronavirus among coronaviruses, and examples thereof include SARS-CoV-2 reported at the end of 2019. The infectious disease caused by SARS-CoV-2 is also called COVID-19. The term "novel coronavirus" naturally encompasses mutants and variants of the known coronavirus. The term "coronavirus infection" naturally encompasses infectious diseases caused by the novel coronavirus, including COVID-19.

EXAMPLES

The present invention will be described using examples, but the present invention is not limited to these.

Test Example 1

A test was performed using a viral infection cell model to evaluate the effect of combination use of a pyrazine derivative and remdesivir. Specifically, the antiviral effect was evaluated by determining the cytopathic effect (CPE). In addition to the CPE assay, the antiviral effect can be evaluated by a viral antigen-antibody method or by real-time polymerase chain reaction (PCR) of virus RNA extracted from a virus culture supernatant.

T-705 was selected as a pyrazine derivative. Remdesivir was selected as another therapeutic agent for coronavirus infection. Novel coronavirus (SARS-CoV-2) was selected as an RNA virus.

(1) Vero E6 Cell Culture

African green monkey kidney Vero E6 cells that were subcultured in a 10% fetal bovine serum-added Eagle minimum essential medium (MEM) containing 60 μg/mL kanamycin (Eagle MEM/kanamycin medium) at 37 °C under the 5% carbon dioxide condition were removed from the culture broth by the trypsin-ethylenediaminetetraacetic acid method, and a suspension containing $2\times10^4$ cells per 100 µL of the medium was prepared and seeded on a 96 well plate. The Vero E6 cells were cultured overnight at 37 °C under the 5% carbon dioxide condition and obtained as a monolayer.

(2) SARS-CoV-2 Infection and Addition of Drugs

A 2% fetal bovine serum-added Eagle MEM/kanamycin medium was used as a test medium. The culture supernatant containing Vero E6 cells obtained in (1) was removed, the following (A) or (B) was added to each well, and the mixture was cultured at 37 °C for 2 hours under the 5% carbon dioxide condition:

(A) 100 µL of SARS-CoV-2 solution prepared with the test medium to obtain a final multiplicity of infection of 0.02

(B) 100 µL of 0.5% DMSO-containing test medium that contained a combination of T-705 and remdesivir at concentrations two-fold the specified concentrations for each combination of the specified concentrations:

Specified concentrations (µM) of T-705:

0, 0.1, 0.3, 1, 3, 10, 30, 100, 300, 1000

Specified concentrations (µM) of remdesivir:

0, 0.1, 0.3, 1, 3, 10, 30, 100

At 2 hours after infection, the culture supernatant was removed from each well, and 100 µL of 0.5% DMSO-containing test medium that contained a combination of T-705 and remdesivir at concentrations one-fold the specified concentration for each combination of the specified concentrations were added. After the drugs were added, the cells were cultured at 37 °C for 2 days under the 5% carbon dioxide condition.

(3) Determination of Cytopathic Effect (CPE)

The CPE associated with proliferation of SARS-CoV-2 was determinated by the following method.

After completion of culture, 25 µL of 100% formalin solution was added to each well to inactivate virus and immobilize cells. The mixture was left stand at room temperature for 2 hours or longer, the aqueous solution was removed, cells were gently washed with water, and then 50 µL of 0.02% methylene blue solution was added to each well, and the mixture was left stand at room temperature for one hour. The aqueous solution was removed, and cells were gently washed with water and then air-dried. Then, absorbance (660 nm) was measured using a microplate reader (Tecan). For anon-infected control, 100 µL of the test medium was added instead of the SARS-CoV-2 solution, the same operations as for the test group were performed, and the absorbance was measured.

A test was performed for two plates (one patient per plate) (eight patients for infected controls and non-infected controls). The value obtained by subtracting the absorbance of the infected control from the absorbance of the non-infected control was used as the value indicating complete inhibition of viral proliferation, and the CPE inhibition rate was calculated for each test by the following formula:

CPE inhibition rate=100×([absorbance after monotherapy or combination use)−(absorbance of infected control])/([absorbance of non-infected control)−(absorbance of infected control])

Microsoft Office Excel 2016 FORECAST function (linear regression) was used to calculate 50% CPE inhibitory concentration.

The 50% CPE inhibitory concentration was confirmed when T-705 and remdesivir were used in combination at concentrations lower than their respective 50% inhibitory concentrations ($IC_{50}$) of monotherapy.

In addition to remdesivir, the same test as described above was performed for the therapeutic agents for coronavirus infection listed in Table 1. The $IC_{50}$ was confirmed when T-705 and remdesivir were used in combination at concentrations lower than their respective $IC_{50}$ of monotherapy.

TABLE 1-1

| No. | Name |
|---|---|
| [Table 1-1] | |
| 1 | Interferon α-2A |
| 2 | Interferon α-2B |
| 3 | Interferon α-n1 |
| 4 | Interferon α-n3 |
| 5 | Interferon β-1a |
| 6 | Interferon β-1b |
| 7 | Acyclovir |
| 8 | Ganciclovir |
| 9 | Ribavirin |
| 10 | Taribavirin |
| 11 | Indinavir |
| 12 | Nelfinavir |
| 13 | Saquinavir |
| 14 | Camostat |
| 15 | Lopinavir/ritonavir combination (brand name, Kaletra) |
| 16 | Epigallocatechin gallate |
| 17 | Kaempferol-7-glucoside |
| 18 | Mycophenolic acid |
| 19 | Darunavir |
| 20 | Mercaptopurine |
| 21 | Disulfiram |
| 22 | Tenofovir disoproxil |
| 23 | Dolutegravir |
| 24 | Boceprevir |
| 25 | Andrographolide |
| 26 | Luteolin |
| 27 | Baicalein |
| 28 | Sofosbuvir |
| 29 | Dactinomycin |
| 30 | Galidesivir |
| 31 | Baloxavir marboxil |
| 32 | Oseltamivir |
| 33 | Zanamivir |
| 34 | Valsartan |
| 35 | Telmisartan |
| [Table 1-2] | |
| 36 | Losartan |
| 37 | Irbesartan |
| 38 | Azilsartan |
| 39 | Olmesartan |
| 40 | Emodin |
| 41 | Baicalin |
| 42 | Chloroquine |
| 43 | Hydroxychloroquine |
| 44 | Griffithsin |
| 45 | Quinine |
| 46 | Lactoferrin |
| 47 | Baricitinib |
| 48 | Sunitinib |
| 49 | Erlotinib |
| 50 | Fedratinib |
| 51 | Gefitinib |
| 52 | Silibinin |
| 53 | 3,4-Dichloroisocoumarin |
| 54 | Ligustrazine |
| 55 | Statin |
| 56 | Melatonin |
| 57 | Eplerenone |
| 58 | Methylprednisolone |
| 59 | Salvianolic acid B |
| 60 | MOL736 |
| 61 | Chelidocystatin |
| 62 | Astaxanthin |
| 63 | Curcumin |

TABLE 1-1-continued

| No. | Name |
|---|---|
| 64 | Vitamin D |
| 65 | Valsartan |
| 66 | Bananin |
| 67 | Iodobananin |
| 68 | Vanillinbananin |
| 69 | Eubananin |
| 70 | Silvestrol |
| 71 | β-glucan |
| | [Table 1-3] |
| 72 | Vitamin A |
| 73 | Vitexin |
| 74 | Gossypol |
| 75 | Toremifene |
| 76 | Equilin |
| 77 | Ciclesonide |
| 78 | Amantadine |
| 79 | Foscarnet |
| 80 | Triazavirin |
| 81 | Umifenovir |
| 82 | Rapamycin |
| 83 | Everolimus |
| 84 | Nitazoxanide |
| 85 | Tizoxanide |
| 86 | Caraphenol A |
| | [Table 1-4] |
| 87 | Dexamethasone |
| 88 | Nafamostat |
| 89 | Ivermectin |
| 90 | Molnupiravir |
| 91 | Sangibamycin |
| 92 | AT-527 |
| 93 | PF-07321332 |
| 94 | VIR-2703 |
| 95 | Tocilizumab |
| 96 | Bamlanivimab |
| 97 | Etesebimab |
| 98 | Kasiribimab/Imdebimab |
| 99 | AZD7422 |
| 100 | VIR-7831 |
| 101 | VIR-7832 |
| 102 | BI 767551 |

Test Example 2

T-705 was selected as a pyrazine derivative. Remdesivir was selected as another therapeutic agent for coronavirus infection. Human coronavirus (HCoV-OC43) responsible for common cold, which belongs to the genus betacoronavirus as with the novel coronavirus, was selected as an RNA virus.

(1) Culture of BHK-21 Cells

Hamster kidney BHK-21 cells that were subcultured in a 10% fetal bovine serum-added EMEM containing 60 μg/mL kanamycin (EMEM/kanamycin medium) at 37 °C under the 5% carbon dioxide condition were removed from the culture broth by the trypsin-ethylenediaminetetraacetic acid method, then a suspension containing $4\times10^4$ cells per 100 μL in the medium was prepared and seeded on a 96 well plate. The BHK-21 cells were cultured overnight at 37 °C under the 5% carbon dioxide condition and obtained as a monolayer.

(2) HCoV-OC43 Infection and Addition of Drugs

A 2% fetal bovine serum-added EMEM/kanamycin medium was used as a test medium. The culture supernatant containing BHK-21 cells obtained in (1) was removed, the following (A) to (C) were added:

(A) 100 μL of the test medium (B) 50 μL of HCoV-OC43 solution prepared with the test medium to obtain a final infectivity titer of $4.0\times10^3$ $TCID_{50}$ (C) 50 μL of 1% DMSO containing test medium that contained a combination of T-705 and remdesivir at concentrations four-fold the specified concentrations for each combination of the specified concentrations:

| | |
|---|---|
| Specified concentration (μM) of T-705: | 0, 1, 10, 100, 1000 |
| Specified concentration (μM) of remdesivir: | 0, 0.1, 0.3 |

After the drugs were added, the cells were cultured at 33 °C for 3 to 4 days under the 5% carbon dioxide condition.

(3) Determination of Cytopathic Effect (CPE)

The CPE associated with proliferation of HCoV-OC43 was assessed by the following method.

After completion of culture, 50 μL of 100% formalin solution was added to each well to inactivate virus and immobilized cells. The mixture was left stand at room temperature for 2 hours or longer, the aqueous solution was removed, and cells were gently washed with water, and then 50 μL of 0.02% methylene blue solution was added to each well, and the mixture was left stand at room temperature for one hour. The aqueous solution was removed, and cells were gently washed with water and then air-dried. Then, absorbance at 660 nm was measured using a microplate reader (Tecan). For anon-infected control, 50 μL of the test medium was added instead of the HCoV-OC43 solution, the same operations as for the test group were performed, and the absorbance was measured.

A test was performed for two plates (one patient per plate) (six patients for infected controls and non-infected controls). The value obtained by subtracting the absorbance of the infected control from the absorbance of the non-infected control was used as the value indicating complete inhibition of viral proliferation, and the CPE inhibition rate was calculated for each test by the following formula:

CPE inhibition rate=100×([absorbance after monotherapy or combination use)−(absorbance of infected control])/([absorbance of non-infected control)−(absorbance of infected control])

Microsoft Office Excel 2016 FORECAST function (linear regression) was used to calculate 50% CPE inhibitory concentration.

The CPE inhibition rates on single use or combination use of drug(s) were compared. A CPE inhibition rate on single use of 1000 μM of T-705 was 79%, and a CPE inhibition rate on each of the single use of 0.1 μM and 0.3 μM of remdesivir was 51% and 80%, respectively. In contrast, a CPE inhibition rate on each of combination use of 1000 μM of T-705 and 0.1 μM or 0.3 μM of remdesivir were 92% and 102%, respectively.

The combination use increased the CPE inhibition rate compared to each of single use of T-705 and remdesivir, and almost 100% of CPE inhibition effect thereof was confirmed. Also, on the basis of this result, it is considered that drugs having a mechanism of action similar to remdesivir, namely reverse transcriptase inhibitors and/or RNA polymerase inhibitors (for example, molnupiravir) are also effective in combination with T-705.

INDUSTRIAL APPLICABILITY

A therapeutic agent for coronavirus infection comprising a combination of a pyrazine derivative or a salt thereof and another therapeutic agent for coronavirus infection is useful in the field of pharmaceutical industry.

The invention claimed is:

1. A pharmaceutical composition for treating COVID-19, comprising favipiravir or a salt thereof, and remdesivir.

2. A method for treating COVID-19, comprising administering favipiravir or a salt thereof and remdesivir.

* * * * *